US012733916B2

(12) United States Patent
Zinnanti

(10) Patent No.: US 12,733,916 B2
(45) Date of Patent: Sep. 15, 2026

(54) MODULAR FORCEPS

(71) Applicant: William J. Zinnanti, Santa Cruz, CA (US)

(72) Inventor: William J. Zinnanti, Santa Cruz, CA (US)

( * ) Notice: Subject to any disclaimer, the term of this patent is extended or adjusted under 35 U.S.C. 154(b) by 577 days.

(21) Appl. No.: 18/205,100

(22) Filed: Jun. 2, 2023

(65) Prior Publication Data

US 2023/0389907 A1 Dec. 7, 2023

Related U.S. Application Data

(60) Provisional application No. 63/348,313, filed on Jun. 2, 2022.

(51) Int. Cl.
*A61B 10/06* (2006.01)

(52) U.S. Cl.
CPC .................................... *A61B 10/06* (2013.01)

(58) Field of Classification Search
CPC .... A61B 17/2909; A61B 17/128–1285; A61B 2017/291–2925; A61B 2017/2926–2946; A61B 2017/0046–00473; A61B 2017/0488–049
See application file for complete search history.

(56) References Cited

U.S. PATENT DOCUMENTS

| | | | | |
|---|---|---|---|---|
| 2,790,437 A * | 4/1957 | Moore | A61B 10/06 | 600/564 |
| 5,308,358 A * | 5/1994 | Bond | A61B 17/29 | 606/174 |
| 5,368,606 A * | 11/1994 | Marlow | A61B 17/29 | 606/174 |
| 5,665,100 A * | 9/1997 | Yoon | A61B 17/1285 | 606/205 |
| 5,782,748 A * | 7/1998 | Palmer | A61B 10/06 | 606/205 |
| 6,139,563 A | 10/2000 | Cosgrove, III et al. | | |
| 7,771,425 B2 | 8/2010 | Dycus et al. | | |
| 7,819,894 B2 | 10/2010 | Mitsuishi et al. | | |
| 8,043,328 B2 * | 10/2011 | Hahnen | A61B 17/07207 | 606/205 |

(Continued)

FOREIGN PATENT DOCUMENTS

| | | |
|---|---|---|
| CN | 100566672 C | 12/2009 |
| WO | WO2010104755 | 9/2010 |

*Primary Examiner* — Elizabeth Houston
*Assistant Examiner* — Jonathan A Hollm
(74) *Attorney, Agent, or Firm* — Douglas B Teaney; CARDINAL LAW GROUP, LLC

(57) ABSTRACT

A forceps system including a handle. The handle includes an immovable proximal handgrip and a lever resiliently pivotably coupled to the immovable proximal handgrip, such that exertion of a manual gripping force on the lever pivots the lever in a proximal direction toward the handgrip. A shaft and jaw assembly is releasably couplable to the handle, the shaft and jaw assembly including a pair of pivotable jaw members normally biased to an open configuration, the open configuration of the jaws corresponding to a released configuration of the handle, the jaws being moved to a closed configuration upon the exertion of the manual gripping force on the lever, pivoting the lever toward the handgrip.

13 Claims, 12 Drawing Sheets

(56) References Cited

U.S. PATENT DOCUMENTS

| | | | |
|---|---|---|---|
| 8,211,119 | B2 | 7/2012 | Palmer et al. |
| 11,147,613 | B2 | 10/2021 | Soni |
| 2001/0034536 | A1 | 10/2001 | Looper et al. |
| 2009/0318830 | A1 | 12/2009 | George et al. |
| 2019/0133596 | A1 | 5/2019 | Brodaczewski et al. |

* cited by examiner

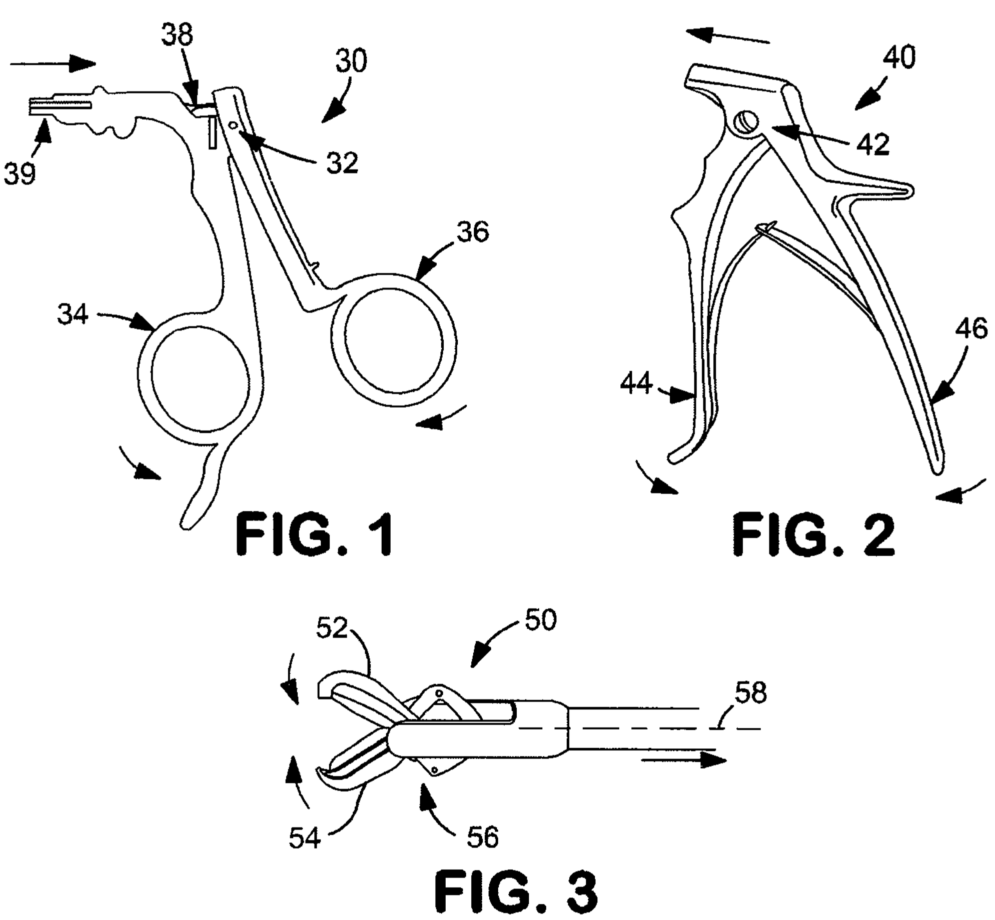
FIG. 1
FIG. 2
FIG. 3
Disposable flexible biopsy forceps passing through endoscope channel
Biopsy forceps
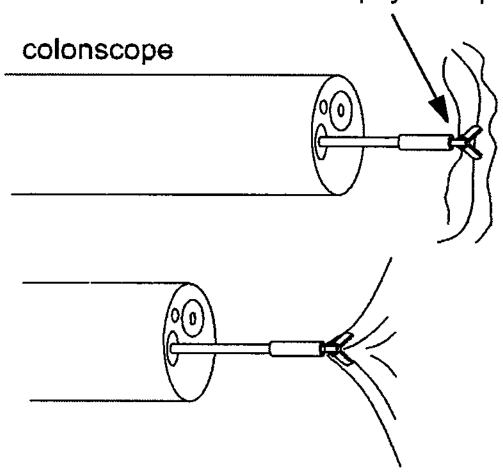
FIG. 4

100

100
104
102

112
108
106
86
114
100
114
102

86
92
94
88

220
260
210
258
252
254
256
258

248
246

244
242

212

266
250
264

133
244
242

217
262
216
135
110
250
137

MODULAR FORCEPS

This application claims priority, under 35 USC 119(e), of the filing date of U.S. 63/348,313, filed Jun. 2, 2022, the complete disclosure of which is hereby expressly incorporated herein by reference.

TECHNICAL FIELD

The invention relates to forceps used for medical surgical procedures.

BACKGROUND OF THE INVENTION

Biopsy is a common procedure of collecting a sample from biologic tissue to assess for the presence, cause, or extent of a disease. Tissues samples are commonly collected by forceps with sharp jaws. These forceps are used to snip off the sample from surrounding tissue. Biopsy forceps include a handle, extending shaft and collection jaws. The forceps may be reusable or disposable. Disposable forceps are preferable to provide a clean sharp set of jaws for each procedure. The extended shaft of currently available biopsy forceps is commonly ridged. Malleable versions are not detachable or single use. A ridged shaft limits access to target tissue and visualization. Therefore, biopsy forceps with a reusable handle and single use detachable malleable shaft is desirable to provide clean sharp biopsy jaws for each procedure with improved visualization and tissue access. This device can provide advantages not currently available including reduced cost and efficiency.

Biopsy of biologic tissue is a common minimal invasive procedure performed to assess tissue structure or the presence, cause, and extent of a disease. The goal of the procedure is to obtain an adequate sample while preserving the surrounding tissue. Optimum biopsies preserve the structure of the target tissue. This feature is especially important for the identification of individual layers in multilayer tissue samples. Biopsies are commonly performed with a sharp jaw forceps. The sharpness of the jaws allows for a clean cut and reduces or prevents the need to pull or tear the sample from surrounding tissue. Pulling or tearing of the tissue commonly causes more pain and bleeding during the procedure. Biopsies are often taken from tissue within a cavity. Small cavities restrict space and visualization of the tissue. Additionally, newer diagnostic modalities and equipment incorporating scopes and cameras that require direct line of site to obtain good visualization of tissues. A biopsy forceps with a malleable shaft can be bent into position and hold the position to maximize visualization and provide access to desired target tissue that may be otherwise unobtainable with a straight shaft.

Biopsy forceps with extended shafts commonly utilize an outer shaft tube and inner wire or rod mechanism to transfer mechanical force between the handle and jaws. The outer tube is fixed to the more distal portion of the handle while the inner rod is connected to the more proximal side. The two handle parts are connected at a pivot point and rotate relative to each other. The two basic designs of the handles provide a push or pull of the inner rod depending on whether the handle parts cross (FIG. 2) or not (FIG. 1) at the pivot point. Similarly, the biopsy jaw parts rotate relative to each other at a pivot point and close or open depending on whether the jaw parts cross or not at the pivot point. One common type of biopsy jaws employs a "double action" mechanism where jaws comprise four parts that cross rotate at two separate pivot points (FIG. 3). This mechanism provides symmetric action of the biopsy jaws where a pull of the inner rod causes the jaws to close. For each different design, closure of the handle provides closure of the forceps. This action is intuitive to the operator as the hand is closed to close the jaws of the forceps. Currently available biopsy forceps with an attachable detachable shaft and jaws are made of metal and built to withstand repeated use and sterilization. This type of sterilizable forceps employs a "push" type handle that forces the inner actuator rod forward to close the biopsy jaws. This robust construction of the shaft is too expensive for single use and cannot be made of malleable materials due to the force needed to push the distal jaws closed. Disposable forms of this biopsy forceps are made with permanently fixed plastic handles and cannot be made of malleable materials due to the required force needed to close the jaws. A second form of biopsy forceps employs a pull action to close the jaws. This shaft of this device can be made of flexible materials. The currently available devices are flexible but not malleable and will not hold a shape. This type of flexible biopsy forceps is commonly passed down a channel of a flexible endoscope (FIG. 4).

SUMMARY OF THE INVENTION

In an embodiment, disclosed are biopsy forceps with a reusable handle and attachable detachable single use shaft and jaws. This design utilizes a flexible internal actuator wire and a malleable outer shaft that can be bent into different shapes and hold position in the bent shape. This shaft and jaws can be made to be attached and detached from either push or push handle types. The shaft and jaws for use with a pull type handle can be made with attachment means between the outer tube to the distal portion of the handle and inner actuator rod or wire to the proximal portion. The shaft and jaw design for use with a push type handle requires a mechanism to convert the push force of the handle to a pull force on the inner actuator wire as the outer shaft tube is held in place. This can be accomplished by employing an attachment means between the outer shaft tube and proximal portion of the handle. The internal actuator wire can be shorter than the outer shaft tube and connect to the distal portion of the handle by a structure that slides over the outer shaft tube and connects to the inner actuating wire through an elongated opening or slot in the shaft tube. This outer structure is attached to the distal portion of the handle and provide a pull force on the internal actuating wire as it slides backwards relative to the shaft tube when the handle is closed.

An embodiment of the invention comprises a forceps system. A handle is provided, with proximal and distal handgrip sections pivotably coupled to one another at a pivot axis, a coupler structure disposed at an end of the proximal handgrip section, a biasing element mechanically disposed between the proximal and distal handgrip sections, such that proximal and distal handgrip sections are biased pivotably away from one another, the proximal handgrip section having a first end comprising a gripping portion and a second end opposite the first end comprising a coupling structure, the distal handgrip section having a first end comprising a gripping portion and a second end opposite the first end comprising a coupling structure, the pivot axis connecting the proximal and distal handgrip sections between their respective gripping portions and coupling structures, such that pivoting movement of the gripping portions of the proximal and distal handgrip sections toward one another against the biasing element corresponds to pivoting movement of the coupling structures of the proximal and distal handgrip sections away from one another. An extension has a longitudinal axis, a first end releasably couplable to the coupling structures of the proximal and distal handgrip portions, and a second end having a connector disposed thereon. An end effector is releasably couplable to the second end of the extension.

In an embodiment, the end effector including a first jaw and a second jaw, wherein at least one of the first and second jaws is pivotable about a pivot axis extending substantially perpendicular to the extension longitudinal axis. The handle, extension, and end effector in an operably coupled state, the biasing element prompting the first and second jaws toward an open configuration, the open configuration of the jaws corresponding to a released configuration of the handle, a closed configuration of the jaws corresponding to a gripped configuration of the proximal and distal handgrip portions, wherein the proximal and distal handgrip portions pivoted toward one another against the biasing element.

In an embodiment, the extension and end effector are preferably fabricated from materials which enable the extension and end effector to be fabricated in a sterile state, but which enable the extension and end effector to be at least one of discarded or recycled after use.

In an embodiment, at least one of the extension and end effector are fabricated from materials which are relatively stiff yet bendable with a modest exertion of manually-applied force, and shape-retaining once bent or formed into a desired configuration.

In an embodiment, the extension comprises a core surrounded by a sheath, the core and sheath being axially relatively movable, the core releasably couplable to the proximal handgrip portion and the sheath releasably couplable to the distal handgrip portion. In an embodiment, the coupling structure of the proximal handgrip portion comprises a hollow tubular region having an externally-threaded surface; and the core is releasably couplable to the proximal handgrip portion via an internally-threaded collar that is rotatably coupled to, but axially-fixed in relation to, the first end of the extension. In an embodiment, the core, in turn, comprises a central tension member slidably coupled relative to a surrounding tube. In an embodiment, the central tension member comprises one of a semi-rigid shaft, a wire, a braided cable.

In an embodiment, the coupling structure of the distal handgrip portion comprises a fork structure thereat, receivable within the hollow tubular region of the proximal handgrip portion, through a slot in a sidewall thereto, for arcuate reciprocating movement therein, in response to gripping and release of the handle by an operator thereof. A pin is coupled to the sheath of the extension, for axial movement therewith. A slider is axially movable within the hollow tubular region and pivotably coupled to the fork structure. The pin may have a key structure at a proximal end thereof, receivable within a corresponding key-shaped recess in a distal end of the slider, through a similar key-shaped slot a sidewall of the hollow tubular region. The key-shaped slot may be located in the externally-threaded surface of the hollow tubular region.

In an embodiment, wherein the sheath moves axially distally or proximally in response to the gripping portions of the proximal and distal handgrip sections being squeezed together or released, respectively, distal axial movement of the sheath, relative to the core, causing a pulling force to be exerted by the core on the jaws of the end effector prompting the jaws into a closed configuration.

In an embodiment, the end effector is releasably coupled to the extension.

In an embodiment of the invention, the extension is configured to be bent from an original straight configuration into a desired shape and then restored to its original configuration, through at least two cycles of bending and restoration, to facilitate multiple uses of the forceps system in multiple medical procedures. In an embodiment of the invention, the end effector is one of: permanently affixed to the extension; replaceably attachable to the extension to enable a variety of end effectors having different configurations to be employed with a single extension and handle.

BRIEF DESCRIPTION OF THE DRAWINGS

FIG. 1 is a side elevation of a prior art pull-type forceps handle.

FIG. 2 is a side elevation of a prior art push-type forceps handle.

FIG. 3 is a side perspective view of a prior art pull-type double-acting jaw end effector.

FIG. 4 is an illustration of an exemplary method of use of biopsy forceps.

DETAILED DESCRIPTION OF THE DRAWINGS

Figure 5:
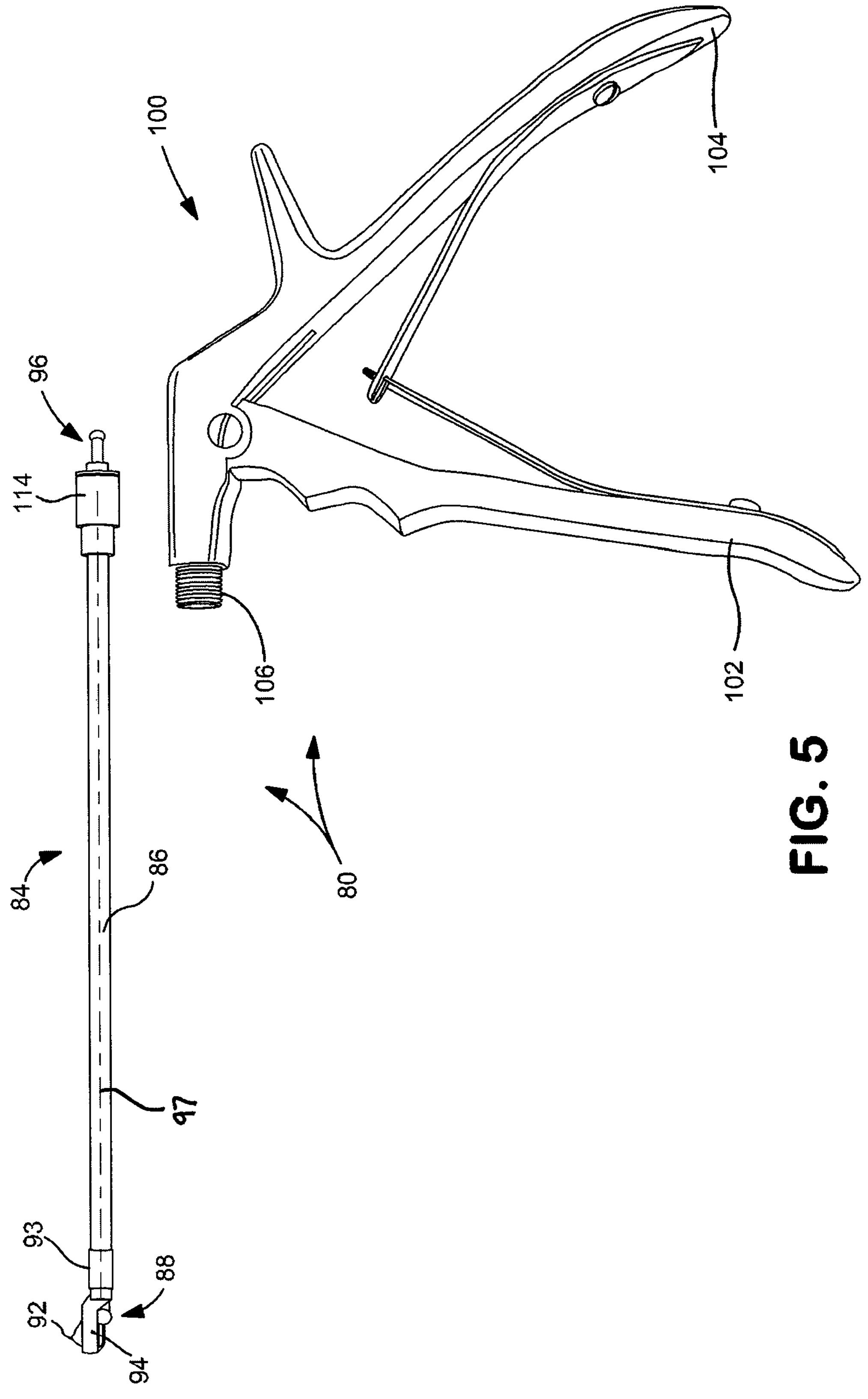
FIG. 5 is a side elevation of components of a forceps according to an embodiment of the present invention.

While this invention is susceptible of embodiment in many different forms, there are shown in the drawings and described in detail herein, specific embodiments, with the understanding that the present disclosure is to be considered as an exemplification of the principles of the invention and is not intended to limit the invention to the embodiment(s) illustrated.

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims. Unless specifically noted, it is intended that the words and phrases in the specification and the claims be given their plain, ordinary and accustomed meaning to those of ordinary skill in the applicable arts. It is noted that the inventors can be their own lexicographers. The inventors expressly elect, as their own lexicographers, to use only the plain and ordinary meaning of terms in the specification and claims unless they clearly state otherwise and then further, expressly set forth the “special” definition of that term and explain how it differs from the plain and ordinary meaning. Absent such clear statements of intent to apply a “special” definition, it is the inventors’ intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f) or pre-AIA 35 U.S.C. § 112~6. Thus, the use of the words “function,” “means” or “step” in the Detailed Description of the Invention or claims is not intended to somehow indicate a desire to invoke the special provisions of 35 U.S.C. § 112(f) or pre-AIA 35 U.S.C. § 112~6 to define the invention. To the contrary, if the provisions of 35 U.S.C. § 112(f) or pre-AIA 35 U.S.C. § 112~6 are sought to be invoked to define the inventions, the claims will specifically and expressly state the exact phrases “means for” or “step for” and the specific function (e.g., “means for roasting”), without also reciting in such phrases any structure, material or act in support of the function. Thus, even when the claims recite a “means for . . . ” or “step for . . . ” if the claims also recite any structure, material or acts in support of that means or step, or that perform the recited function, then it is the clear intention of the inventor not to invoke the provisions of 35 U.S.C. § 112(f) or pre-AIA 35 U.S.C. § 112~6. Moreover, even if the provisions of 35 U.S.C. § 112(f) or pre-AIA 35 U.S.C. § 112~6 are invoked to define the claimed inventions, it is intended that the inventions not be limited only to the specific structure, material or acts that are described in the illustrated embodiments, but in addition, include any and all structures, materials or acts that perform the claimed function as described in alternative embodiments or forms of the invention, or that are well known present or later-developed, equivalent structures, material or acts for performing the claimed function.

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and apparatus are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, apparatus and technologies to which the disclosed inventions may be applied. Thus, the full scope of the inventions is not limited to the examples that are described below.

Various aspects of the present invention may be described in terms of functional block components and various processing steps. Such functional blocks may be realized by any number of hardware or software components configured to perform the specified functions and achieve the various results.

Various representative implementations of the present invention may be applied to any system performing laparoscopic surgery. Thus, while there are disclosed improved apparatus, systems, and methods for fabrication of biopsy forceps, the principles are applicable to apparatus, systems and methods not disclosed herein. Similarly, references to methods are also applicable of systems and apparatus, which perform the processes in the operation of the recited apparatus. It will be appreciated that numerous changes may be made to the present invention without departing from the scope of the claims, including but not limited to combinations of elements or structures of the various illustrated embodiments. For example, while specific materials and/or methods of manufacture of the apparatuses described herein may be discussed, it is understood that one having ordinary skill in the art may select different materials and/or methods of manufacture, as desired or necessary to meet the requirements of a particular application, without departing from the scope of the present invention.

FIGS. 1-2 illustrate examples of known basic designs of forceps handles that provide a pull (handle 30, FIG. 1) or push force (handle 40, FIG. 2) on an inner actuating rod to open or close the biopsy jaws. In pull-type handle 30, FIG. 1, application of squeeze force to cause handle pieces 34, 36 pivot about axis 32, to move relatively toward one another, as indicated by the arrows, causing the top portion of the left (distal) handle piece 34 to move away from the right (proximal) handle piece 36, such that the top end of 36 “pulls” a central wire 38 coupled thereto, relative to an outer tube 39. In push-type handle 40 (FIG. 2), application of squeeze force causes handle pieces 44, 46 to pivot about axis 42, with the lower ends to move relatively toward one another, as indicated by the arrows, which causes the top portion of left (distal) handle piece 44, which is interior to the top of the right (proximal) handle piece and thus not visible, to move toward the left or in the distal direction relative to proximal handle piece 46, thus causing the top end of handle piece 44 to push an inner rod (not shown) towards the left, relative to proximal handle piece 46. Specifically, in such a push-type forceps, an extension (not shown) can be permanently affixed or detachably attached to the handle, and an end effector, comprising one (usually lower) jaw is fixed, and an another (usually upper) jaw, is pivotable, and the upper jaw is normally open until the handle is squeezed. The structure between the jaws and the handle comprises the extension, wherein the upper half of the extension slides, in its entirety, relative to the lower half of the extension. A tang or similar structure extends from the upper movable jaw that rides in a slot in the lower jaw, and causes the pivoting of the jaw, based on the relative movement of the upper and lower halves of the extension. In addition, due to this structure, the extension is not flexible to any meaningful degree, FIG. 3 illustrates a typical prior art biopsy jaws 50, including individual jaw pieces 52, 54, with double action scissor mechanism 56 requiring a pull (rightward arrow) of the internal actuator shaft or wire 58 (shown in broken line) for the jaw pieces to close.

FIG. 4 illustrates typical methods of use of biopsy forceps.

FIG. 5 illustrates components of a biopsy forceps 80 according to an embodiment of the invention. Forceps 80 includes handle 100 and extension 84 with shaft 86, and end effector 88, which, in FIG. 5, is illustrated as having a single moving jaw 92 and a fixed jaw 94. End effector may be permanently fixed or replaceably coupled to shaft 86, e.g., via a threaded connection between collar 93 and shaft 86. Opposite to end effector 88 is coupling 96. In a preferred embodiment of the invention, extension 84, and the components comprising extension 84 (as discussed in further detail hereinafter), are fabricated from flexible yet durable materials, which will allow the extension to be bent, as desired, and retain the shape into which the extension 84 has been formed, subject to being bent back into an original configuration. Such flexibility may be provided or enhanced by the provision of slots or gaps along the lengths of the extension (e.g., in the case of an outer tube(s)) and/or the use of flexible single-strand wire or rod, or braided wire or rope (e.g., for central members). Once assembled, tube 86, which is fixedly coupled to fixed jaw 94, is movably coupled to pin 96 and in turn, handle 102. Moving jaw 92 is, in turn coupled to internally threaded collar 114, e.g., via a stiff or semi-rigid wire or cable 97 extending along a hollow interior of shaft 86. Collar 114 and shaft 86 are in axially slidable relation to one another.

Figure 6:
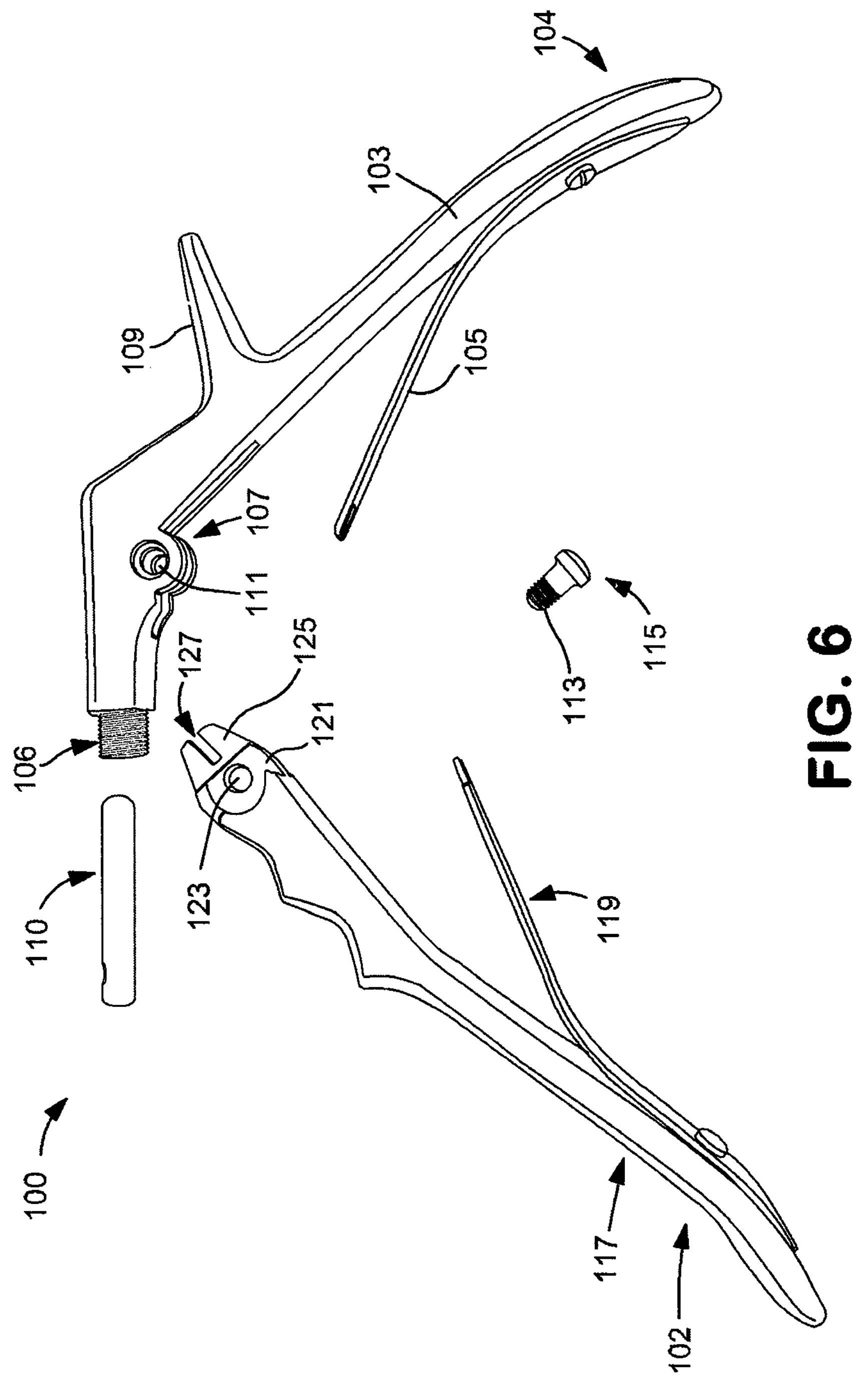
FIG. 6 is a side elevation of a handle thereof, disassembled.
Figure 7:
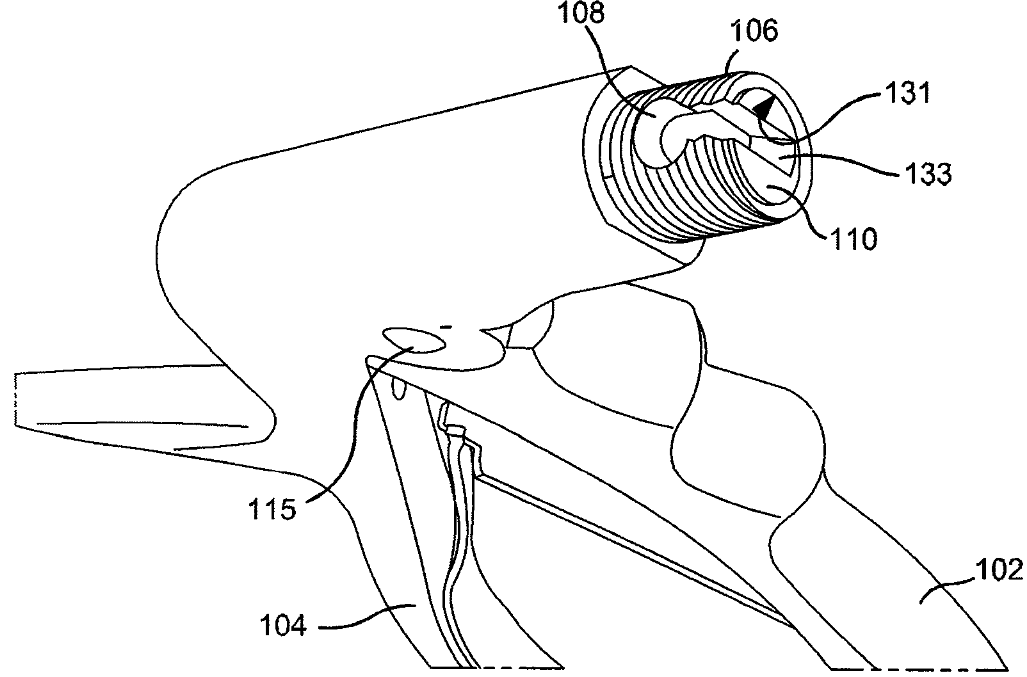
FIG. 7 is a perspective end view of the handle thereof.

FIG. 6-7 illustrate details of handle 100. Proximal grip member 104 includes palm gripping portion 103, proximal spring leaf 105 and ears 107, and thumb webbing catch 109. Spring leaf 105 may be affixed to grip member 104 by any suitable mechanism, e.g., a screw or rivet (not shown). Each ear 107 includes a through-bore 111, one of which, in an embodiment, is threaded, to receive threads 113 of fastener 115. Lever 102 includes finger grip surface 117, distal spring leaf 119, recesses 121 (one on each side of lever 102) with smooth through-bore 123, and fork 125. Spring leaf 119 may be affixed to lever 102 by any suitable mechanism, e.g., a screw or rivet (not shown). Threaded collar 106 surrounds a bore 131 (FIG. 7) which slidingly receives slider 110. Slider 110 includes a further slot 135 (shown in FIG. 29), spanned by cross-bar 137, which engages and is received within notch 127 of fork 125.

Figures 8, 9, 10:
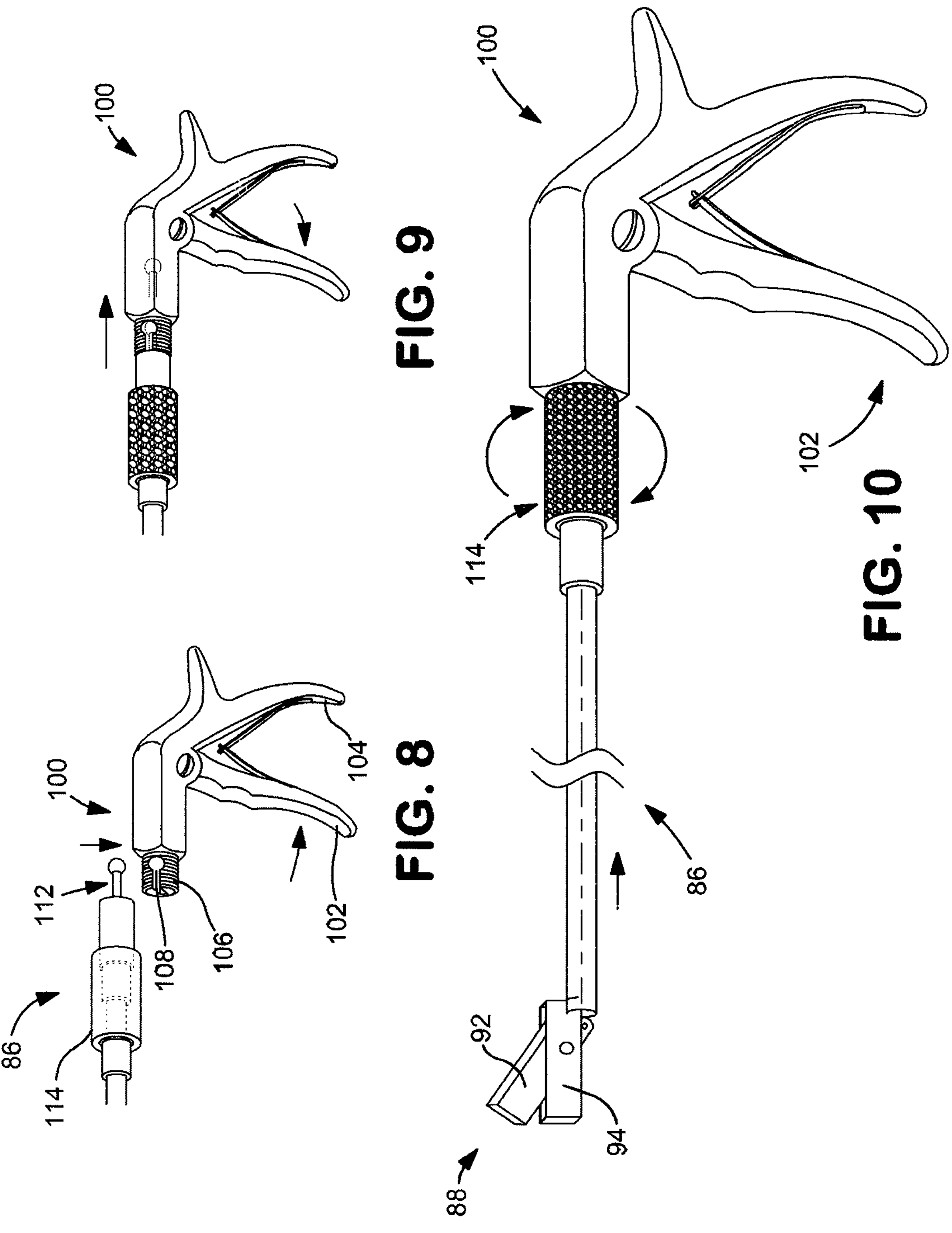
FIG. 8 is an illustration of a step in coupling an extension to a handle.
FIG. 9 is an illustration of a further step thereof.
FIG. 10 is an illustration of a further step thereof.

FIG. 8-10 illustrate a method for attaching extension 84 to handle 100. FIG. 8 illustrates handle 100, with movable distal lever 102 pulled back toward fixed proximal grip member 104. This compression or pulling of lever 102 causes slider 110 (FIG. 6-7) in bore at an upper end of lever 102 to move forward (to the left in FIG. 8). Handle 100 further includes an externally-threaded collar 106 having a generally keyhole shaped side slot 108. Slider 110 includes slot 133 which, when viewed from above, as a similar outline as slot 108. Accordingly, when slider 110 is in its forward position. Slots 108 and 133 align, to accommodate beaded end 112 of extension 84. Release of lever 102 (FIG. 9) causes the slider of lever 102 to move to the right, inwardly, pulling beaded end 112 with it into the interior of the handle 100 as shown in FIG. 9. Internally-threaded collar 114 is slid to the right, to engage externally-threaded collar 106, as shown in FIG. 10.

Figures 11, 12, 13:
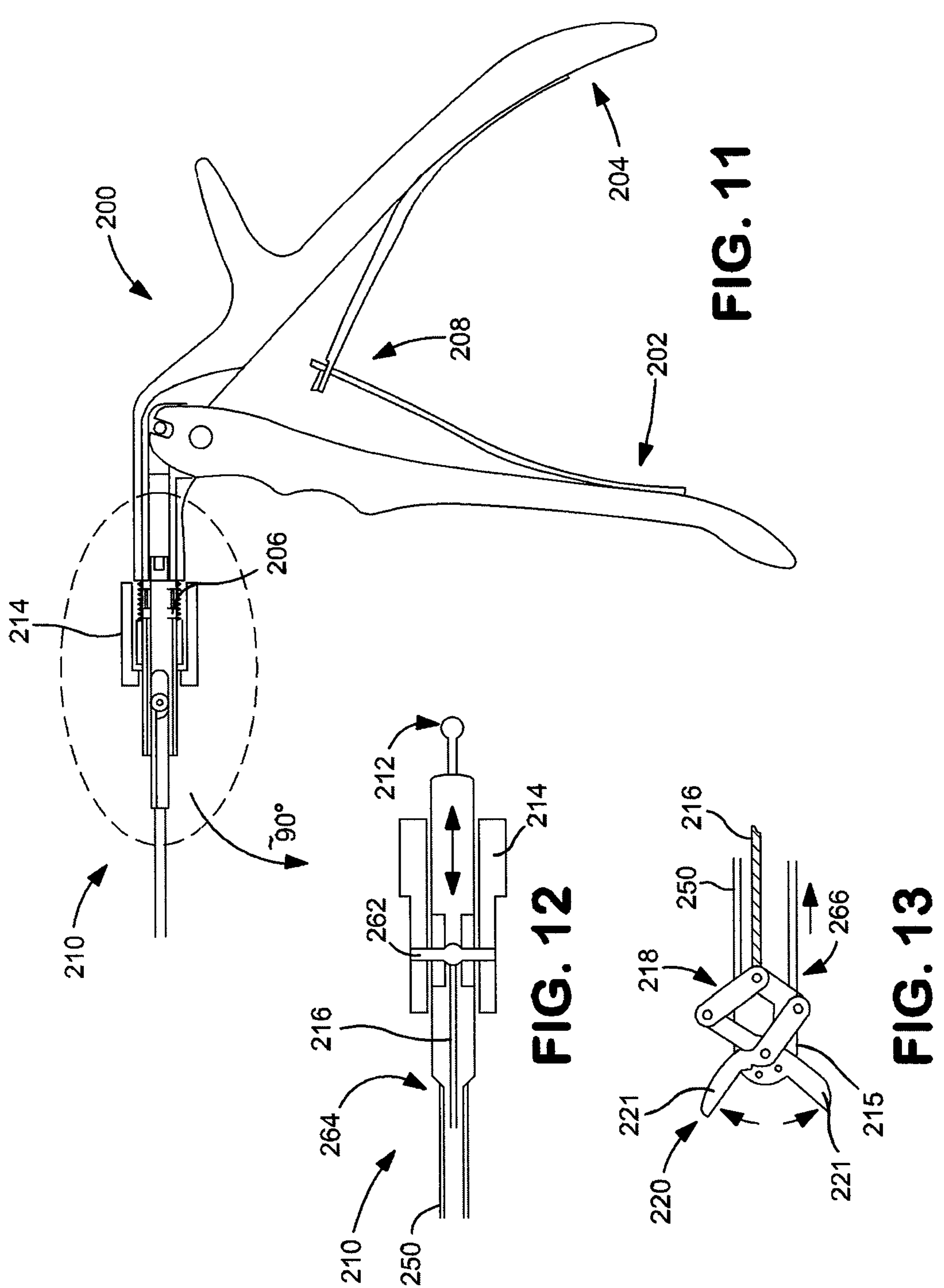
FIG. 11 is a side elevation, partly in section, of a handle coupled to an extension.
FIG. 12 is an enhanced view of a proximal end of an extension.
FIG. 13 is a sectional view of an end effector.

FIG. 11-13 illustrate, in partial side section, components of a push-type forceps, similar to the embodiment of FIG. 5-10, with the jaws in the open configuration, according to an embodiment of the invention. FIG. 11 illustrates a handle 200 together with a flexible shaft and jaw assembly (or extension) 210, as previously described, with internally threaded collar 214. Handle 200 includes movable lever 202, fixed grip portion 204 and threaded collar 206. FIG. 12 illustrates the proximal end of shaft and jaw assembly 210, with internally-threaded collar 214 omitted. FIG. 12 further illustrates the proximal portion of shaft and jaw assembly 210 rotated 90 degrees, relative to the side elevation of FIG. 11. Core wire or cable 216 is fixedly coupled, via pin 262, to FIG. 13 illustrates end effector 220, having jaws 221, and housing 215. In an embodiment of the invention, housing 215 is monolithically formed or permanently affixed to tube 250; in alternate embodiments, housing 215 may be releasably coupled to tube 250, with core wire or cable 216 likewise releasably coupled to the proximal portion of the scissor mechanism illustrated in FIG. 13 for jaws 221 of end effector 220. Releasing lever 202 allows handle spring arrangement 208 to move lever 202 and grip 204 apart to the released or "at rest" orientation, which, in turn, causes elongated tube 250 to move toward the right (from the perspective of FIG. 13 as indicated by the arrow). As core wire/cable 216 has some stiffness, it pushes on the proximal end link of linkage 218 to collapse linkage 218 laterally and spread "vertically" (again relative to FIG. 13), opening jaws 220.

Figures 14, 15, 16, 17:
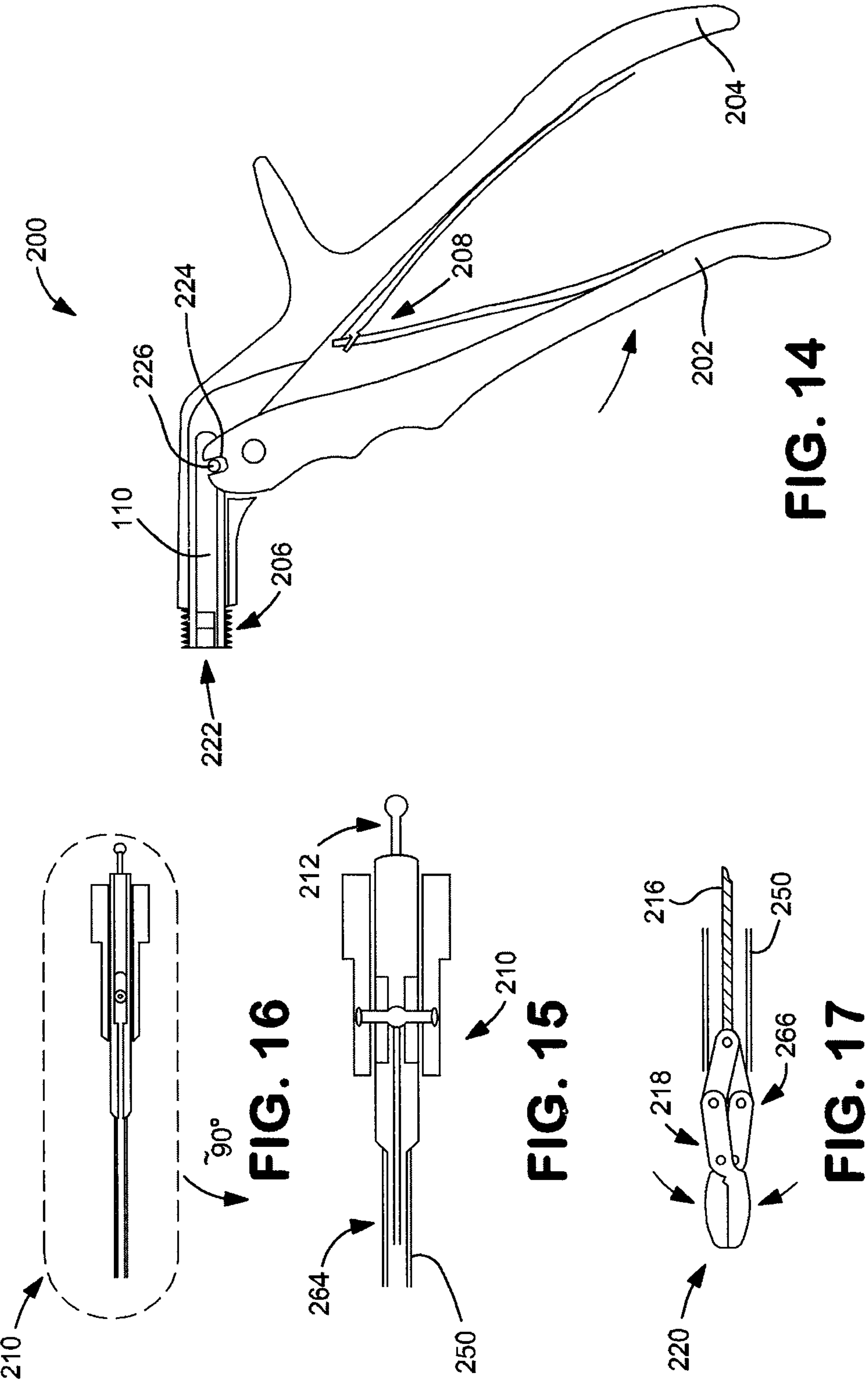
FIG. 14 is a side elevation, partly in section, of a handle in the squeezed configuration.
FIG. 15 is an enlarged sectional view of a coupling of an extension.
FIG. 16 is a view thereof, rotated 90 degrees about a longitudinal axis there.
FIG. 17 is a view of an end effector in a closed configuration.
Figure 18:
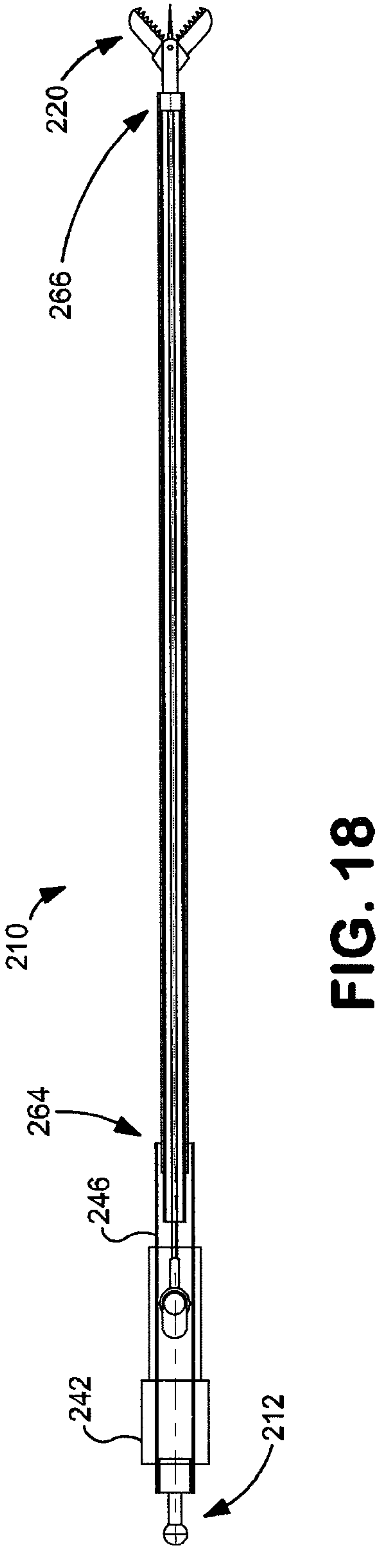
FIG. 18 is a side elevation partly in section of a core of an extension, with end effector.
Figures 19, 20, 21, 22, 23:
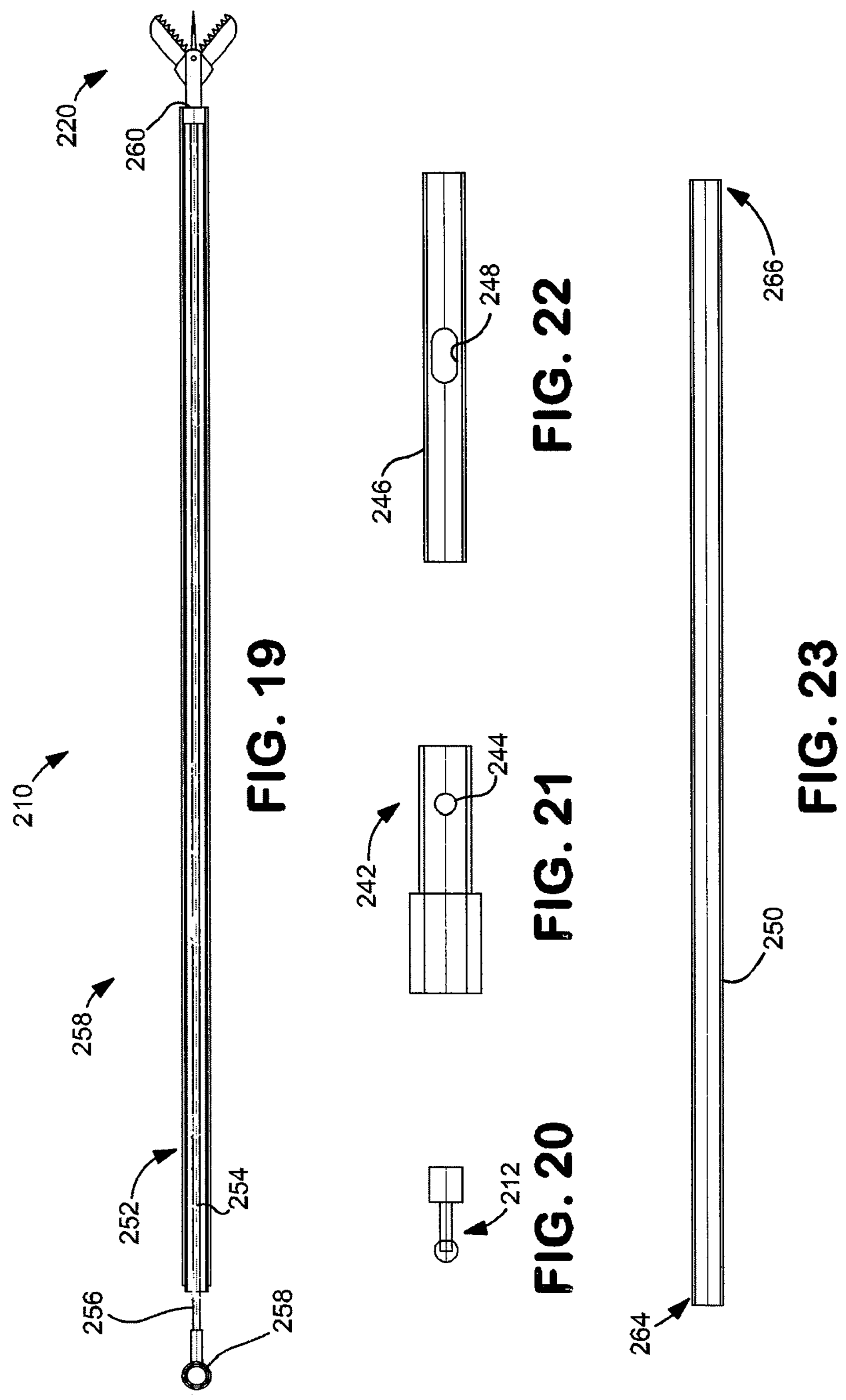
FIG. 19 is a further view thereof.
FIG. 20 is a view of a coupler pin.
FIG. 21 is a view of a threaded collar.
FIG. 22 is a view of a sliding sleeve.
FIG. 23 is a view of an outer tube of the core.

FIG. 14-17 illustrate, in partial side-section, components of the push-type forceps of FIG. 11-13, with the jaws in the closed configuration, according to an embodiment of the invention. Handle 200 includes lever 202, having a slot 224, which receives a pin 226 attached to or emanating from, a slider 110, such that when lever 202 is squeezed, slider 110 moves from right to left from the perspective of FIG. 14, moving tube 250, and in turn housing 215, to move in a distal direction, against the "pull" of static core cable 216, causing jaws 220 to close, as shown in FIG. 17. FIG. 15 illustrates the proximal portion of shaft and jaw assembly 210 rotated 90 degrees, relative to the side elevation of FIG. 16.

FIGS. 18-23 illustrate components for the modular flexible (and/or bendable and shape-retaining) shaft and jaws, similar to that shown in FIG. 11-17. Shaft and jaw assembly 210 includes a core, comprising main body 252 which may include a braided wire 254, straight wire 256, loop 258. A plug 260 with jaws 220 extending therefrom, defines the distal end of shaft and jaw assembly 210. Jaws are configured for relative pivoting movement between closed (FIG. 17) and open (FIG. 13) orientations, with jaws 220 biased to an open orientation through the action of spring 208. Shaft and jaw assembly 210 further includes bead section 212, fixed sleeve 242 having circular openings 244 on diametrically opposed sides thereof, sliding sleeve 246 having elongated openings 248 on diametrically opposed sides thereof, and elongated sliding tube 250. Sliding tube 250 includes proximal end 264 and distal end 266, as shown in FIG. 18-23, 26-27. Sliding sleeve 246 is insertably received within fixed sleeve 242 and fixedly coupled for movement with tube 250, and a proximal end of the core (210 minus plug 260 and jaws 220). Assembly 220 further includes pin 262, which passes through loop 256, elongated openings 248, and has its ends situated at or within openings 244.

Further details of the interaction of pin 262 and loop 256 are discussed hereinafter with respect to FIG. 28. With respect to FIGS. 18 and 19, end 266 of tube 250 is coupled to the housing of jaws 220, for axial movement therewith. Core cable/wire 254 (shown in FIG. 19) is fixedly coupled to a proximal end of a scissor mechanism for jaws 220, and is likewise fixedly coupled to fixed sleeve 242. To complete assembly, fixed sleeve 242 is captured axially by internally threaded collar 214. In an alternative embodiment, sliding sleeve 246 and tube 250 may be fabricated as a single monolithically formed structure.

In operation, once shaft and jaw assembly 210 is coupled to a handle 200, in the manner described above, bead section 212 and slider 110 are locked together in simultaneous axial movement. When lever 202 and grip 204 are squeezed together, slider 110 is moved in a distal direction, together with bead section 212. Bead section 212 in turn pushes sliding sleeve 246 in a distal direction, together with elongated tube 250 and jaws 220. The distal movement of tube 250 is axially relative to core 254, which pulls on the scissor linkage for jaws 220 and causes them to close. When pressure on lever 202 is released, spring arrangement 208 pushes lever 202 toward a distal position relative to grip 204. This causes slider 110 and bead section 212 to move proximally toward grip 204. Elongated tube 250 is in turn moved proximally, in the reverse direction as previously described. Inasmuch as core cable 254, while flexible has some axial stiffness, and is of course enclosed in a narrow tube, core cable 254 will push on the linkage, collapsing it axially and causing the jaws to open. Tube 250, sliding sleeve 246 and bead section 212 may be coupled together using any suitable mechanism, such as force-fit, crimping, spot-welding, brazing, etc.

Figure 24:
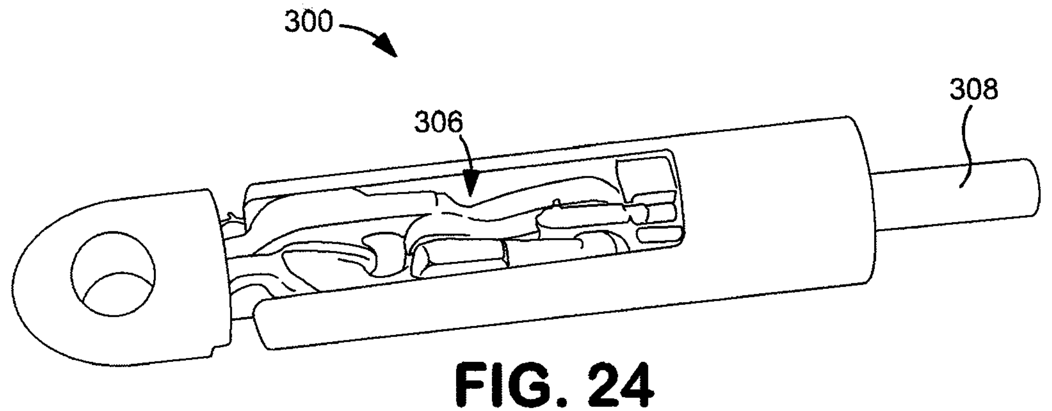
FIG. 24 is a view of an end effector in closed configuration.
Figure 25:
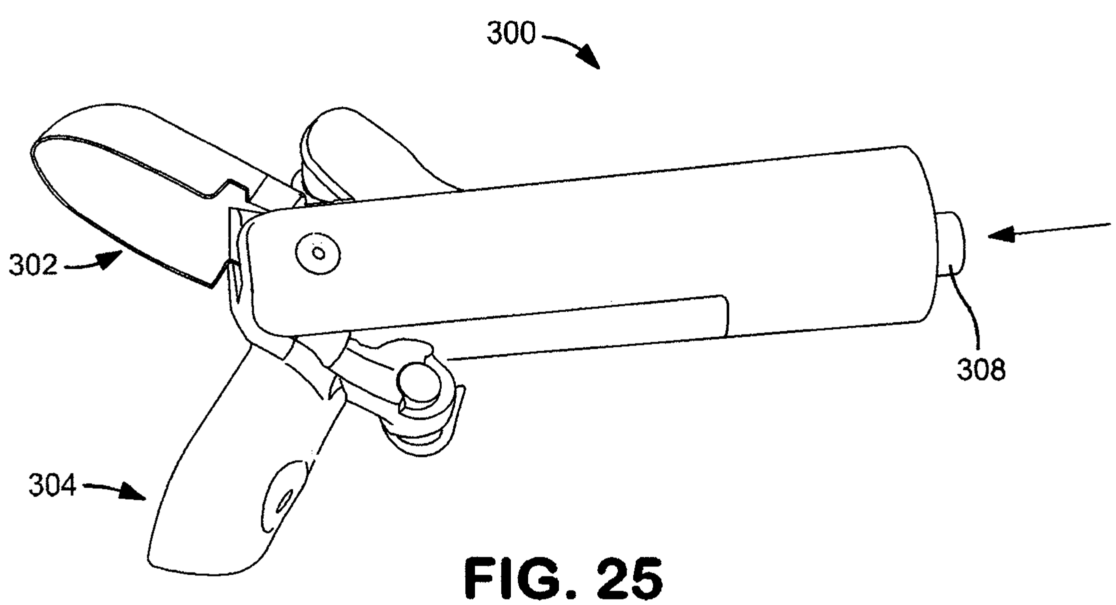
FIG. 25 is a view of an end effector in open configuration.
Figure 26:
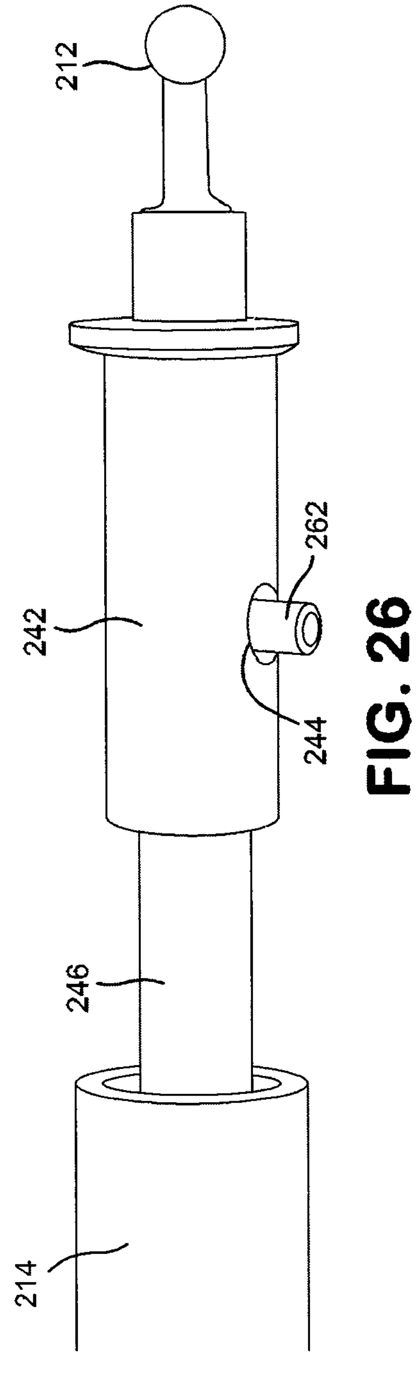
FIG. 26 is a side view of the coupling region for an extension.
Figure 27:
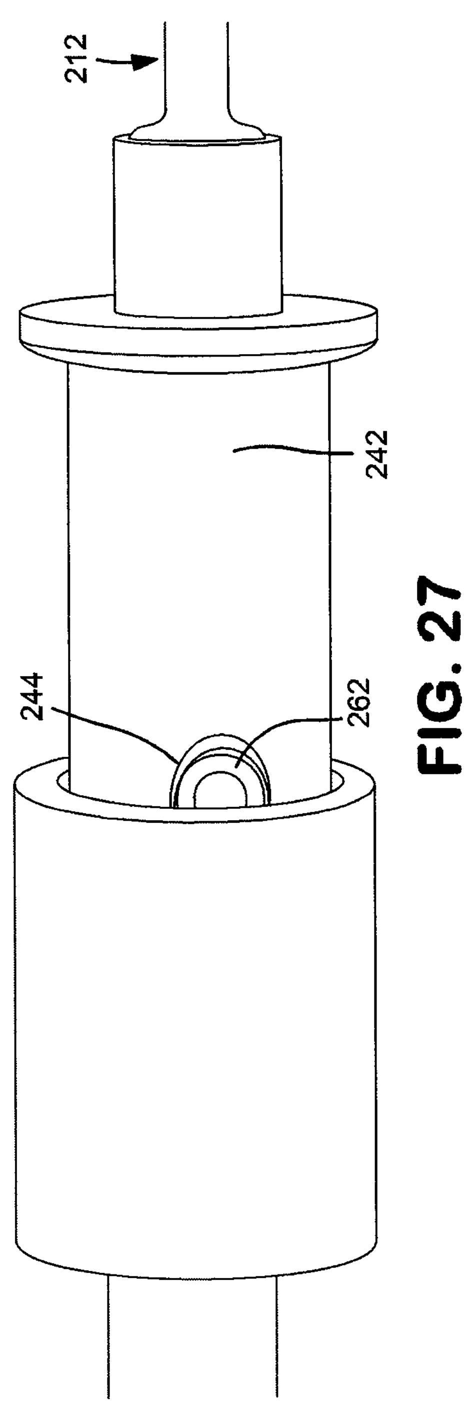
FIG. 27 is a further view thereof.

In a preferred embodiment, the components comprising shaft and jaw assembly 210 are fabricated from materials which are relatively stiff yet bendable with a modest exertion of manually-applied force, and shape-retaining once bent or formed into a desired configuration. Further, the components comprising handle 200 preferably are fabricated from durable, sterilizable materials, such as are known in the art, while the components comprising shaft and jaw assembly 210 may be fabricated either as sterilizable and reusable, or from materials which enable shaft and jaw assembly to be fabricated in a sterile state, but which may be readily discarded and/or recycled, FIG. 24-25 illustrate a double-action, dual jaw end effector 300 having jaws 302, 304 and a scissor mechanism 306 coupled to post 308, such that when post 308 is pushed in a distal direction (arrow), jaws 302, 304 open, and when post 308 is pulled in a proximal direction, jaws 302, 304 close. Post 308 may be couplable to a core cable or wire using any suitable mechanism, such as a threaded coupling, snap fit, hook, etc.

Figures 28, 29:
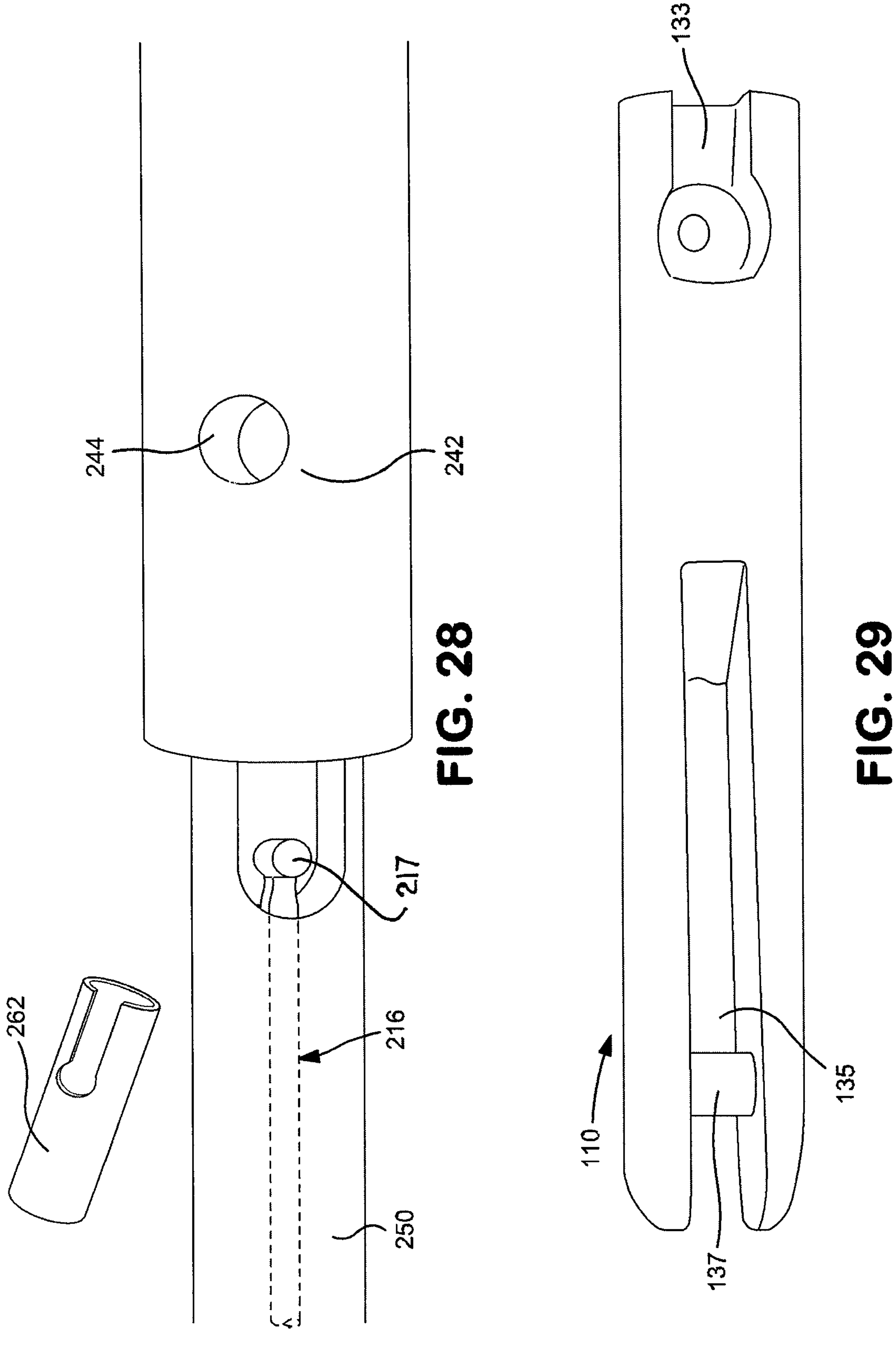
FIG. 28 is an enlarged view of the mechanism for affixing the core cable or wire to the handle housing.
FIG. 29 is a side view of a slider.

FIG. 28 is an enlarged view of fixed sleeve 242, sliding tube 250, core wire 216 (similar or identical to core cable 254 elsewhere described) having a barrel plug 217 at a proximal end thereof, and tubular pin 262, which has an axial slot therein. To assemble core wire 216 to fixed sleeve 242, core wire 216 is inserted into tube 250 until barrel plug 217 becomes aligned with the openings in fixed sleeve 242. Pin 262 is then inserted through the openings in sleeve 242 with its slot aligned with core wire 216, such that barrel plug 217 is captured in the interior of pin 262.

The forceps system of the present invention enables a known push-type forceps handle to be used with a shaft and jaw assembly which provides for gripping action while the handle of the push-type forceps handle is squeezed.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

Although the invention has been described with reference to the above examples, it will be understood that many modifications and variations are contemplated within the true spirit and scope of the embodiments of the invention as disclosed herein. Many modifications and other embodiments of the invention set forth herein will come to mind to one skilled in the art to which the invention pertains having the benefit of the teachings presented in the foregoing descriptions and the associated drawings. Therefore, it is to be understood that the invention shall not be limited to the specific embodiments disclosed and that modifications and other embodiments are intended and contemplated to be included within the scope of the appended claims. Although specific terms are employed herein, they are used in a generic and descriptive sense only and not for purposes of limitation.

What is claimed is:

1. A forceps system, comprising:

a handle, with proximal and distal handgrip sections pivotably coupled to one another at a pivot axis, a coupler structure disposed at an end of the proximal handgrip section, a biasing element mechanically disposed between the proximal and distal handgrip sections, such that proximal and distal handgrip sections are biased pivotably away from one another, the proximal handgrip section having a first end comprising a gripping portion and a second end opposite the first end comprising a coupling structure, the distal handgrip section having a first end comprising a gripping portion and a second end opposite the first end comprising a coupling structure, the pivot axis connecting the proximal and distal handgrip sections between their respective gripping portions and coupling structures, such that pivoting movement of the gripping portions of the proximal and distal handgrip sections toward one another against the biasing element corresponds to pivoting movement of the coupling structures of the proximal and distal handgrip sections away from one another;

an extension, having a longitudinal axis, a first end releasably couplable to the coupling structures of the proximal and distal handgrip portions, and a second end having a connector disposed thereon; and an end effector releasably couplable to the second end of the extension;

the end effector including a first jaw and a second jaw, wherein at least one of the first and second jaws is pivotable about a pivot axis extending substantially perpendicular to the extension longitudinal axis, the extension comprising a core surrounded by a sheath, the core and sheath being axially relatively movable, the core releasably couplable to the proximal handgrip portion and the sheath releasably couplable to the distal handgrip portion;

the sheath being coupled to the distal handgrip section, so that the sheath is pushed in a distal direction, when the distal handgrip section is moved in a proximal direction toward the proximal handgrip section, the sheath directly contacting the first and second jaws to move them into a closed configuration, the core, in its operable configuration when coupled to the proximal handgrip section, being axially fixed and immovable relative to the proximal handgrip section.

2. The forceps system of claim 1, further comprising the handle, extension, and end effector in an operably coupled state, the biasing element prompting the first and second jaws toward an open configuration, the open configuration of the jaws corresponding to a released configuration of the handle, a closed configuration of the jaws corresponding to a gripped configuration of the proximal and distal handgrip portions, wherein the proximal and distal handgrip portions pivoted toward one another against the biasing element.

3. The forceps system according to claim 1, further comprising the extension and end effector fabricated from materials which enable the extension and end effector to be fabricated in a sterile state, but which enable the extension and end effector to be at least one of discarded or recycled after use.

4. The forceps system according to claim 1, further comprising at least one of the extension and end effector being fabricated from materials which are relatively stiff yet bendable with a manually-applied force, and shape-retaining once bent or formed into a desired configuration.

5. The forceps system according to claim 1, wherein the coupling structure of the proximal handgrip portion comprises a hollow tubular region having an externally-threaded surface; and the core releasably couplable to the proximal handgrip portion via an internally-threaded collar that is rotatably coupled to, but axially-fixed in relation to, the first end of the extension.

6. The forceps system according to claim 5, wherein the coupling structure of the distal handgrip portion comprises a fork structure thereat, receivable within the hollow tubular region of the proximal handgrip portion, through a slot in a sidewall thereto, for arcuate reciprocating movement therein, in response to gripping and release of the handle by an operator thereof;

a pin is coupled to the sheath of the extension, for axial movement therewith;

a slider is axially movable within the hollow tubular region and pivotably coupled to the fork structure;

the pin having a key structure at a proximal end thereof, receivable within a corresponding key-shaped recess in a distal end of the slider, through a similar key-shaped slot in a sidewall of the hollow tubular region.

7. The forceps system according to claim 6, wherein the key-shaped slot is located in the externally-threaded surface of the hollow tubular region.

8. The forceps system according to claim 5, wherein the core, in turn, comprises a central tension member slidably coupled relative to a surrounding tube.

9. The forceps system according to claim 8, wherein the central tension member comprises one of a semi-rigid shaft, a wire, a braided cable.

10. The forceps system according to claim 9, wherein a proximal end of the tension member is coupled to the internally-threaded collar, precluding relative axial movement therebetween.

11. The forceps system according to claim 1, wherein the end effector is releasably coupled to the extension.

12. The forceps system according to claim 1, wherein the extension is configured to be bent from an original straight configuration into a desired shape and then restored to its original configuration, through at least two cycles of bending and restoration, to facilitate multiple uses of the forceps system in multiple medical procedures.

13. A forceps system, comprising:

a handle, with proximal and distal handgrip sections pivotably coupled to one another at a pivot axis, a coupler structure disposed at an end of the proximal handgrip section, a biasing element mechanically disposed between the proximal and distal handgrip sections, such that proximal and distal handgrip sections are biased pivotably away from one another, the proximal handgrip section having a first end comprising a gripping portion and a second end opposite the first end comprising a coupling structure, the distal handgrip section having a first end comprising a gripping portion and a second end opposite the first end comprising a coupling structure, the pivot axis connecting the proximal and distal handgrip sections between their respective gripping portions and coupling structures, such that pivoting movement of the gripping portions of the proximal and distal handgrip sections toward one another against the biasing element corresponds to pivoting movement of the coupling structures of the proximal and distal handgrip sections away from one another;

an extension, having a longitudinal axis, a first end releasably couplable to the coupling structures of the proximal and distal handgrip portions, and a second end having a connector disposed thereon; and an end effector, permanently affixed to the extension;

the end effector including a first jaw and a second jaw, wherein at least one of the first and second jaws is pivotable about a pivot axis extending substantially perpendicular to the extension longitudinal axis, the extension comprising a core surrounded by a sheath, the core and sheath being axially relatively movable, the core releasably couplable to the proximal handgrip portion and the sheath releasably couplable to the distal handgrip portion;

the sheath being coupled to the distal handgrip section, so that the sheath is pushed in a distal direction, when the distal handgrip section is moved in a proximal direction toward the proximal handgrip section, the sheath directly contacting the first and second jaws to move them into a closed configuration, the core, in its operable configuration when coupled to the proximal handgrip section, being axially fixed and immovable relative to the proximal handgrip section.

* * * * *